(12) United States Patent
Galante et al.

(10) Patent No.: US 7,759,096 B2
(45) Date of Patent: Jul. 20, 2010

(54) PROCESS FOR ENZYMATIC PRODUCTION OF TRIGLYCERIDES

(75) Inventors: Jenifer Heydinger Galante, Oakland, NJ (US); Steven L. Clauss, Manville, NJ (US); Randal J. Bernhardt, Antioch, IL (US); Alfred K. Schultz, Maple Glen, PA (US)

(73) Assignee: Stepan Company, Northfield, IL (US)

( * ) Notice: Subject to any disclaimer, the term of this patent is extended or adjusted under 35 U.S.C. 154(b) by 328 days.

(21) Appl. No.: 10/585,427

(22) PCT Filed: Jan. 29, 2004

(86) PCT No.: PCT/US2004/002511

§ 371 (c)(1),
(2), (4) Date: Feb. 5, 2009

(87) PCT Pub. No.: WO2005/081669

PCT Pub. Date: Sep. 9, 2005

(65) Prior Publication Data

US 2009/0131701 A1    May 21, 2009

(51) Int. Cl.
    *C12P 7/64* (2006.01)
(52) U.S. Cl. ..................................... 435/134
(58) Field of Classification Search .................. 435/134; 554/219
    See application file for complete search history.

(56) References Cited

U.S. PATENT DOCUMENTS

| 4,381,264 | A | 4/1983 | Struve |
| 6,136,985 | A | 10/2000 | Millis |
| 6,361,980 | B2 * | 3/2002 | Sugiura et al. ............... 435/134 |
| 6,420,577 | B1 | 7/2002 | Reaney et al. |
| 6,897,327 | B2 | 5/2005 | Rongione et al. |

FOREIGN PATENT DOCUMENTS

| GB | 1577933 | 10/1980 |
| WO | WO 91/16443 | 10/1991 |
| WO | WO 99/32105 | 7/1999 |
| WO | WO 00/18944 | 4/2000 |

OTHER PUBLICATIONS

Study of the Lipase-Catayzed Synthesis of Triolein, Biotechnology and Bioengineering, vol. 41, No. 11 (May 1993), pp. 1021-1026, John Wiley & Sons, Inc.
Francoise Ergan, et al., "Effect of Lipase Specificity on Triglyceride Synthesis", Biotechnology Letters, vol. 13, No. 1 (1991), pp. 19-24.
F. Ergan, et al., "Production of Glycerides from Glycerol and Fatty Acid by Immobilized Lipases in Non-aqueous Media", Biotechnology and Bioengineering, vol. 35, (Jan. 1990), pp. 195-200, John Wiley & Sons, Inc.
F. Ergan, et al., "Solvent Free Triglyceride Synthesis Using Lipozyme™ IM-20", Biotechnology Letters, vol. 10, No. 9, (1988) pp. 629-634.
MacRae, A. R. Lipase-Catalyzed Interesterification of Oils and Fats, JAOCS Feb. 1983, vol. 60, No. 2, pp. 291-294.
International Search Report (PCT/US04/02511) dated Aug. 17, 2007.

* cited by examiner

*Primary Examiner*—Deborah D Carr
(74) *Attorney, Agent, or Firm*—McAndrews, Held & Malloy, Ltd.

(57) ABSTRACT

A process for enzymatic production of glyceride compositions, specifically industrially practicable production of triglycerides, including conjugated linoleic and linolenic acid triglycerides, and the compositions produced by such process. An enzymatic reaction zone is first utilized, in which a mixture of glycerol and fatty acids or fatty acid derivatives is reacted in the presence of an enzymatic catalyst to form 1,3 diglycerides. The mixture is then circulated through a second thermal rearrangement zone, maintained at a higher temperature, to promote rearrangement of the 1,3 diglycerides to 1,2 diglycerides. Triglycerides are produced by re-circulating the mixture through the enzymatic production zone.

15 Claims, No Drawings

PROCESS FOR ENZYMATIC PRODUCTION OF TRIGLYCERIDES

FIELD OF THE INVENTION

The invention relates to a process for producing fatty acid glycerides, specifically for enzymatic production of triglycerides, including conjugated linoleic and linolenic acid triglycerides, which decreases production reaction time, increases reaction vessel utilization, and reduces production energy usage.

BACKGROUND OF THE INVENTION

Glycerides are fatty acid esters of the triol glycerol. Specifically, triglycerides (or triacylglycerols), are fatty acid esters in which all three of the glycerol —OH groups have been esterified by fatty acids. Some of the many uses of triglycerides include utilization as a fat source in a variety of specialized nutritional products; carriers for flavors, vitamins, essential oils and colors; mineral oil alternatives; moisture barriers; clouding agents for beverages; primary and secondary emollients; lubricants; and solubilizing agents.

Particularly desirable to the nutrition and health-care fields are triglycerides of conjugated linoleic acid and conjugated linolenic acid (collectively known as "CLA"). CLAs have generated much interest in the academic and business communities because of their nutritional, therapeutic, and pharmacological properties. CLAs have become biologically and commercially important as they have been observed to inhibit mutagenesis and to provide unique nutritional value. Additionally, CLAs promote body fat reduction, body weight reduction, increased muscle mass, increased feed efficiency, prevention of weight loss due to immune stimulation, elevated CD-4 and/or CD-8 cell counts in animals, increased bone mineral content, prevention of skeletal abnormalities in animals, and/or decreased blood cholesterol levels. Due to the natural esterases found in mammals, the CLA-ester may be readily cleaved to release the desirable free fatty acid. Therefore, CLA triglycerides are desirable since they are much more stable to oxidation than free fatty acids, thus lending to a longer product shelf-life. Furthermore, CLA glycerides are increasingly fat miscible with increasing CLA acylation. See, e.g., U.S. Pat. No. 6,136,985 (Millis) and WO 00/18944 (Conlinco, Inc.) for discussion of CLA esters and uses thereof. Besides CLAs, however, desirable acyl group donors for production of triglycerides may include other free fatty acids and fatty acid derivatives containing from about 2 to 24 carbon atoms.

Glyceride esters of fatty acids are generally prepared by an esterification reaction of glycerol with a corresponding fatty acid, an alcohol interchange reaction of glycerol with oil or fat, or other similar reactions. The reaction processes can be divided into two groups: chemical reactions, which utilize an acidic or alkali catalyst or the like, and biochemical processes, which utilize fat-hydrolyzing enzymes.

In chemical processes, generally, the first and third hydroxyl positions of the glycerol molecule are acylated first, while the second position is later acylated. This type of reaction to completion is difficult and time-consuming, however. A variety of chemical processes used to prepare esters are generally known to those skilled in the art. These methods include acid-catalyzed reaction of acids and alcohols, alkali-catalyzed transesterification of acyl esters with alcohols, and the like.

An alternative to chemical methodology is the utilization of fat-hydrolyzing enzymes such as various lipases. Fatty acids and/or fatty acid derivatives can be reacted in the presence of solid phase bound lipases. WO 91/16443 (NovoNordisk AS), for example, discloses a method utilizing *Candida antarctica* lipase, *Candida fugosa* lipase, and other enzymes to catalyze formation of triglycerides from fatty acids or their derivatives in combination with glycerol. U.S. Pat. No. 6,361,980 (Sugiura) describes the enzymatic production of 1,3 diglycerides. WO 0018944 (Conlinco, Inc.), WO 9932105 (DCV, Inc.), and U.S. Pat. No. 6,136,985 (Millis) describe the use of enzymes to esterify CLA while GB 1,577,933 describes the use of enzymes to interesterify and incorporate fatty acids into pre-existing triglycerides.

However, the previous processes described above utilize a reaction chamber maintained at a temperature conducive to enzymatic catalyzation. These processes provide no mechanism for isomerization of the 1,3-diglycerides to 1,2-diglycerides. Specifically, no separate higher temperature thermal rearrangement zone is provided.

At temperatures conducive to enzymatic catalysis, meanwhile, the 1,3 selective lipase generally used will esterify the first and third hydroxyl positions first. Further reaction from 1,3 diglycerides to triglycerides will only proceed at a very slow rate, ill-suited to industrial application. Those skilled in the art will recognize that a 1,3 specific lipase has generally not been suitable for catalyzing triglyceride synthesis. See, e.g., F. Ergan et al., "Effect of Lipase Specificity on Trigylceride Synthesis," 13 Biotech. Letters, No. 1, pp. 19-24 (1991) ("Ergan et al."). Ergan et al. states that conventional methods for production of triglycerides using enzymatic catalyzation either produce low triglyceride yield or require very long reaction time, i.e. 6 weeks in some instances. Specifically, Ergan et al. recognize that a means of catalyzing 1,3 diglyceride to 1,2 diglyceride isomerization has been long-felt and required to effectively and efficiently produce triglycerides, but offers no resolution for such a need.

Thus, there is presently a need for a more efficient and industrially practical process for the production of triglycerides, including conjugated linoleic and linolenic acid triglycerides, utilizing at least one enzymatic catalysis zone containing 1,3 specific lipase and at least one thermal rearrangement zone to isomerize 1,3 diglycerides to 1,2 diglycerides to efficiently produce triglycerides, including conjugated linoleic acid triglycerides.

BRIEF SUMMARY OF THE INVENTION

Embodiments of the present process for the production of triglycerides provide one or more of the following advantageous features:

(1) a process for thermally rearranging 1,3 diglycerides produced by enzymatic catalyzation into more reactive 1,2 diglycerides;

(2) a more efficient and more industrially practicable process for the production of triglycerides, including, for example, triglycerides of enriched CLA content;

(3) glyceride compositions, including, for example, a mixture of di- and triglycerides of enriched CLA content, made by a process of enzymatic catalyzation and isomerization;

(4) decreased reaction time, increased vessel utilization, and reduced energy usage; all providing a cost savings; and (5) a mechanism to remove non-glyceride reaction by-product.

Other objects of the presently disclosed technology will become apparent to those skilled in the art who have the benefit of this specification and the prior art.

In one embodiment, there is provided a more efficient process for preparing 1,2-diglyceride esters of fatty acids, which are more reactive and more readily converted to triglycerides than the 1,3-diglycerides generally produced by previously known methods. In the present process, a reaction mixture containing an acyl group acceptor such as glycerol, a monoglyceride, or mixtures thereof is combined with an acyl group donor such as a fatty acid or fatty acid derivative. The reaction mixture is circulated through an enzyme-packed tower, zone A, which includes an enzyme preparation such as a 1,3 lipase to carry out an esterification reaction. A mechanism is provided to remove the non-glyceride reaction by-products, such as water or lower alcohol content.

The mixture from the enzyme reaction zone A is then circulated to a thermal rearrangement zone B, which is maintained at a temperature at least 5° C. above the of the enzymatic reaction zone A. The increased zone B temperature, greater than the mild temperatures conducive to enzymatic reaction, facilitates thermal rearrangement of 1,3-diglycerides to 1,2-diglycerides.

In another embodiment of the present technology, a process is provided for more efficient and more industrially practicable production of triglycerides than previously known methods. The present method first utilizes the above 2-zone process for production of 1,2-diglycerides. A reaction mixture containing glycerol and fatty acids or fatty acids derivatives is circulated through an enzymatic reaction zone A to produce 1,3-diglycerides, and then through a thermal rearrangement zone B to produce 1,2-diglycerides. After processing through the thermal rearrangement zone B, the mixture containing 1,2-diglycerides is subsequently re-circulated through the enzymatic reaction zone. Although not being bound by any particular theory, it is believed that the remaining —OH groups in the 1,2-diglycerides esterify to form triglycerides much more rapidly than esterification of the remaining —OH groups in 1,3-diglyceride.

Additionally, remaining glycerol and monoglycerides will further esterify during re-circulation of the reaction mixture through the enzymatic reaction zone A. It will be appreciated by those skilled in the art that it is an additional embodiment of the present technology to re-circulate the reaction mixture containing glycerol, fatty acids or fatty acid derivatives, and mono, di, and triglycerides through the enzymatic reaction zone A and thermal rearrangement zone B multiple times as necessary to facilitate completion of the reaction to the desired triglyceride reaction product. Re-circulation of the mixture may be sequential or nonsequential.

A further embodiment of the present technology provides a process for preparation of di- and triglyceride esters enriched with conjugated linoleic or linolenic acid (again collectively termed "CLA"). A reaction mixture containing glycerol and CLA is processed as described above for production of triglycerides.

Additional embodiments of the present technology also include the 1,2- and 1,3-diglyceride and triglyceride esters of fatty acids produced by the above processes, and other embodiments as disclosed by the description and examples.

DETAILED DESCRIPTION OF THE INVENTION

Definitions and Conventions

As used herein, "1,3 diglyceride" refers to a diester of glycerol and a fatty acid or fatty acid derivative thereof, that contains acyl groups at the 1 and 3 positions on the glycerol backbone, as represented by the formula:

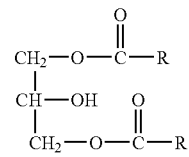

where R is a hydrocarbon chain derived from a fatty acid having from between about 2 and 24 carbon atoms, preferably from about 12 to 20 carbon atoms. Similarly, a "1,2 diglyceride" refers to a diester of glycerol and a fatty acid or fatty acid derivative thereof having acyl groups at the 1 and 2 positions on the glycerol backbone. A "triglyceride" refers to a triester of glycerol and a fatty acid or fatty acid derivative thereof where all three —OH positions on the glycerol triol are esterified. Also as used herein, a triglyceride of a specific fatty acid, such as conjugated linoleic acid, may contain that specific fatty acid at any or all of the three acyl group positions of the triglyceride, while the remaining acyl group positions on the triglyceride are taken up by other fatty acids. Moreover, a triglyceride of a specific fatty acid may contain any of the positional and geometric isomers of that fatty acid.

The term "fatty acid derivative" refers to moieties recognized by one skilled in the art as structures that can be readily converted to carboxylic acids. Examples of such moieties include, but are not limited to: carboxylic acid salts, carboxylic anhydrides, amides, carboxylic esters, ortho esters, 1,3-dioxolanes, dioxanones, oxazoles, and hydrazides.

The term "conjugated fatty acid" refers to any fatty acid containing conjugated double bonds, i.e. two or more double bonds that alternate with single bonds in an unsaturated compound.

The term "conjugated linoleic acid" refers to any conjugated linoleic acid or octadecadienoic free fatty acid containing 18 carbon atoms and two double bonds. It is intended that this term encompass all positional and geometric isomers of linoleic acid with two conjugated carbon-carbon double bonds located at any place in the molecule. Similarly, the term "conjugated linolenic acid" refers to any conjugated linolenic acid containing 18 carbon atoms and three double bonds. The term "CLA" as used herein, collectively encompasses both conjugated linoleic and conjugated linolenic acids. Some examples of CLAs include, but are not limited to the following positional isomers: 7,9-octadecadienoic acid, 9,11-octadecadienoic acid, 10,12-octadecadienoic acid, 11,13-octadecadienoic acid, 9,11,13-octadecatrienoic acid, and 10,12,14-octadecatrienoic acid.

The term "1,3 selective lipase" is intended to mean those lipase enzymes that specifically esterify fatty acids onto the 1 and 3 positions of a glycerol backbone. For example, *Candida clyindracae* lipase is a non-specific lipase enzyme and provides a true randomization of fatty acids on the glyceride positions, whereas *Rhizopus* enzymes have an affinity to the 1,3 positions on the glycerol backbone, affecting the 2-position very little. Enzymes such as *Geotrichum Candidum*, meanwhile, are specific to fatty acids with a double bond in the 9-position, i.e. linoleic acid, regardless of their position on the glycerol backbone.

DESCRIPTION OF THE INVENTION

While the presently described technology will be described in connection with one or more preferred embodiments, it will be understood by those skilled in the art that the presently described technology is not limited to those embodiments. On the contrary, the presently described technology includes all alternatives, modifications, and equivalents as may be included within the spirit and scope of the appended claims.

In one embodiment, there is provided an efficient process with shorter reaction times for preparing 1,2-diglyceride esters of fatty acids, which are more reactive and more readily converted to triglycerides than the 1,3-diglycerides generally produced by previous methods. In the present process, a reaction mixture containing an acyl group acceptor such as glycerol, a monoglyceride, or mixtures thereof is combined with an acyl group donor such as a fatty acid or fatty acid derivative. The reaction mixture is first circulated through an enzyme-packed tower, zone A, which contains an enzyme such as a 1,3 selective lipase, as discussed below, to carry out an esterification reaction. The enzyme packed tower is maintained at a temperature conducive to enzymatic catalyzation. Preferably, this temperature is from about 20° C. to 100° C., more preferably from about 35 to 70° C., and most preferably from about 60 to 70° C.

Again, while not bound to any one theory, it is believed that the product of the enzyme catalyzed esterification reaction from zone A will contain a significant percentage of 1,3-diglycerides as well as monoglycerides, unreacted glycerol, and acyl group donor. At the initiation of the reaction, the 1- or 3-monoglyceride is formed first, followed by the 1,3-diglyceride. Those skilled in the art recognize that triglycerides will form only at more extended reaction times. See, e.g., WO 00/18944 (Conlinco, Inc.); F. Ergan et al., "Effect of Lipase Specificity on Trigylceride Synthesis," 13 Biotech. Letters, No. 1, pp. 19-24 (1991).

The direct esterification reaction is demonstrated by the following chemical formula:

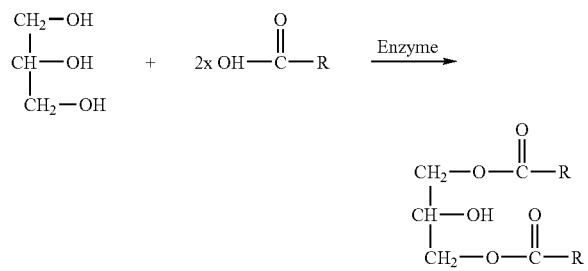

where R is a hydrocarbon chain derived from a fatty acid having between 2 and 24 carbon atoms, preferably between 12 and 20 carbon atoms. Preferred fatty acids for production of glycerides are discussed in further detail below.

After enzymatic reaction in zone A, the reaction mixture is then circulated to a thermal rearrangement zone B, which is preferably maintained at a temperature at least about 5° C. above the temperature of the enzymatic reaction zone A; more preferably, zone B is maintained at least about 20° C. above the temperature of zone A; most preferably, the temperature difference is greater than about 40° C. In one preferred embodiment, the temperature of enzymatic reaction zone A is maintained at about 65° C., and the thermal reaction zone B at about 100° C. It is believed that an increased zone B temperature, greater than the mild temperatures conducive to enzymatic reaction, will facilitate thermal rearrangement of 1,3-diglycerides to 1,2-diglycerides. It is also believed that the 1,2 isomer of diglyceride has a higher entropy value than the 1,3 isomer, and that the remaining —OH group in 1,2-diglyceride is more readily esterified by fatty acids to form a triglyceride.

In another embodiment of the present technology there is provided a more efficient and more industrially practicable process for production of triglycerides than previously known methods. This method first utilizes the above 2-zone process for production of a controlled mixture of 1,3- and 1,2-diglycerides. A reaction mixture, containing glycerol and fatty acids or fatty acids derivatives, is circulated through an enzymatic reaction zone A to produce 1,3-diglycerides, and then through a thermal rearrangement zone B to produce 1,2-diglycerides. After processing through the thermal rearrangement zone B, the reaction mixture containing 1,2-diglycerides is recirculated through the enzymatic reaction zone A.

It is believed that due to the higher entropy value of the 1,2-diglyceride isomer, the remaining —OH group in the 1,2-diglycerides esterify to form triglycerides much more rapidly than esterification of the remaining —OH group in the 1,3-diglyceride. It is also believed that this reaction will normally proceed at least two times faster, and often upwards of ten times faster than production of triglycerides according to conventional methods. See Comparative Example 1, below. The total time for production of the triglycerides, therefore, may proceed at any rate similar to conventional methods. However, preferably, the total time for production of triglycerides is less than 48 hours, more preferably, the total production time is less than 36 hours, and most preferably, less than 30 hours.

Additionally, remaining glycerol and monoglycerides will further esterify during re-circulation of the mixture through the enzymatic reaction zone A. It will be appreciated by those skilled in the art that additional embodiments of the present technology may re-circulate the reaction mixture containing glycerol, fatty acids or fatty acid derivatives, and mono, di, and triglycerides through the enzymatic reaction zone A and thermal rearrangement zone B multiple times as necessary to facilitate completion of the reaction to triglyceride. Whether circulated through the zone A-zone B-zone A cycle one time or numerous times, the reaction may be run until the final yield of triglycerides is upwards of 90%, and often upwards of 95% of the final reaction product.

Preferably, the present technology utilizes a mechanism to remove the non-glyceride reaction by-products such as water or lower alcohols. See, e.g. U.S. Pat. No. 6,361,980 B2 (Sugiura et al.). Sugiura et al. discloses a method for enzymatic production of 1,3-diglyceride while decreasing water or lower alcohol formed by the reaction in a dehydration tank. F. Ergan, et al., "Production of Glycerides from Glycerol and Fatty Acid by Immobilized Lipases in Non-aqueous Media," 35 Biotech. & Bioeng., pp. 195-200 (1990), discloses several methods for by-product removal such as free evaporation, use of molecular sieves or filters, and the use of vacuum. In the present technology, such mechanisms or any other dehydration, vacuum or separation method recognized by those skilled in the art may be utilized either in the enzymatic reaction zone A, the thermal rearrangement zone B, or in a separate zone. Alternatively, unreacted glycerol, fatty acid, and/or fatty acid derivatives can be removed after completion of the reaction by conventional isolation or purification methods such as distillation.

In the enzymatic reaction zone A, any suitable enzyme which esterifies fatty acids and glycerol may be used. Preferably, a lipase is utilized. More preferably, the lipase is selected from one of the following: *Rhizomucor miehi, Candida antarctica, Candida cylindracea, Pseudomonas cepacia, Pseudomonas fluorescens, Candida rugosa, Aspergillus niger,* and *Geotrichum candidum*. Some enzymes will esterify fatty acids on any position of the glycerol backbone, while others react only to esterify specified positions. Yet others are reactive only to specific fatty acid species. For example, *Candida cylindracea* is non-specific and will esterify on any position of the glycerol backbone. Meanwhile, lipases such as *Rhizopus delamar, Rhizopus japonicus, Rhizopus niveus, Aspergillus niger, Mucor javanicus,* and *Mucor miehi* are 1,3-position selective lipases. Preferably, a 1,3 selective lipase is utilized in the present technology. However, it will be understood by those skilled in the art that any of the described enzymes may be utilized. Moreover, only between about 1 and 20% of enzyme is preferably needed based on total weight of the reaction mixture. More preferably, an amount between 2% and 5% of lipase is used. The enzyme is also preferably used a number of times during the presently described reaction processing.

It is also preferred that the enzyme used is immobilized in the presently described technology. Embodiments of the present technology optionally provide a non-reactive matrix to support the enzyme. For example, the enzyme may be immobilized on an ion-exchange resin as disclosed in U.S. Pat. No. 6,361,980 (Sugiura et al.). Immobilized enzymes are commercially available from Novozyme, Inc. Examples of such enzymes include Novozyme 435, Lipozyme RM-IM, and Lipozyme TL-IM.

Immobilized enzymes are preferred in order to prevent circulation of the enzyme from the enzymatic reaction zone A to the thermal rearrangement zone B. While not being bound to any particular theory, it is believed that the temperatures conducive to thermal rearrangement in zone B will often be incompatible with the enzyme used. Additionally, it is preferred to immobilize the enzyme to prevent its disposal with reaction by-products, and to allow multiple runs of the process with the same enzyme. In some embodiments of the present technology, a reaction mixture is repeatedly circulated through both zone A and B.

Alternatively, however, a lipase may be used which is dispersed and agitated throughout the reaction mixture. The enzyme can be stirred in the reactor with the fatty acids and glycerol as a batch process. The so-formed glycerides and unreacted acids and glycerol are then circulated through a heated zone to facilitate the thermal rearrangement of 1,3-diglycerides to 1,2-diglycerides.

In the embodiments of the present technology, any mole ratio of glycerol to fatty acid or fatty acid derivative may be used. However, it is preferred that the mole ratio of fatty acids or fatty acid derivatives to glycerol is about 0.25:1 to 5:1; more preferably, the mole ratio is about 0.5:1 to 3.5:1, and most preferably, the mole ratio is about 1:1 to 3:1. Any excess reactants may be removed according to the methods discussed above.

Additionally, it is also preferred that little or no solvent be added to the reaction mixture. Avoiding the use of a solvent aids in the removal and purification of non-glyceride reaction by-products and excess reactants. However, a solvent such as hexane, octane or petroleum ether may be used in the reaction. Any solvent selected should not affect the enzyme. Additionally, a small amount of water or buffer solution, preferably 0.2 to 1% may be used with the lipase preparation. However, larger percentage weights of water are undesirable because they may promote a reverse hydrolysis reaction.

Any type of saturated or unsaturated, linear or branched fatty acid containing about 2 to 24 carbon atoms may be used in the reaction, preferably with about 12 to 20 carbon atoms. Types of fatty acids which may be used include, but are not limited to: butyric acid, valeric acid, capronic acid, caprylic and capric acid, enanthic acid, pelargonic acid, undecanoic acid, lauric acid, linoleic acid, linolenic acid, myristic acid, palmitic acid, zoomaric acid, stearic acid, oleic acid, elaidic acid, arachidonic acid, eicosapentaenoic acid, and docosahexaenoic acid. Additionally, lower alkyl esters and other fatty acid derivatives may also be used, including carboxylic acid salts, carboxylic anhydrides, amides, carboxylic esters, ortho esters, 1,3-dioxolanes, dioxanones, oxazoles, and hydrazides.

A further embodiment of the present technology utilizes conjugated fatty acids as the acyl group donor. Routes to produce conjugated unsaturated compounds include hydrogenation of fats using a variety of catalysts, isomerization with alkali metal hydroxides, isomerization at high temperatures using alkali catalysts, and other methods known to those skilled in the art. For example, U.S. Pat. No. 4,381,264 (Struve) provides a process to obtain conjugation of the double bonds of various polyunsaturated fatty acids.

Preferably, the embodiments of the present invention utilize conjugated linoleic or linolenic acids (collectively termed "CLA") as the acyl group donor. U.S. Pat. No. 6,420,577 (Reaney, et al.) describes a process for making CLAs by reacting a linoleic acid-rich oil with a base, while in the presence of a catalytic amount of such a base that is in an aqueous medium via simultaneous hydrolysis and isomerization. Alternatively, CLAs may also be produced by conversion of the linoleic acid-rich oil to an alkyl ester which is further purified by some conventional method (usually distillation), with subsequent isomerization of the ester, or any other method known to those skilled in the art. Co-pending U.S. patent application Ser. No. 10/434,011 provides a process to produce a CLA product enriched in desired CLA isomers which includes the steps of isomerization of an alkyl ester of a linoleic containing material, saponification of the resultant CLA-containing fatty acid ester, and then optionally neutralizing the fatty acid salt to produce a CLA-containing fatty acid.

Additionally, any geometric or positional isomers of CLA may be utilized as the fatty acid in the present technology, however, the cis-9, trans-11 and trans-10, cis-12 isomers of CLA are preferred. It is believed, although not bound by any particular theory, that the 9,11-isomer is preferentially taken up and incorporated into the phospholipid fraction of animal tissues and to a lesser extent the 10,12-isomer has also been found to be similarly incorporated. For example, the CLA may preferably contain at least about 40 and upwardly about 45-50% of cis-9, trans-11 and trans-10, cis-12 isomers of CLA. The resultant triglyceride of the presently described technology may contain CLA derived acyl groups on one or all three of the glycerol backbone positions, with other fatty acids contained on any remaining positions. Preferably, however, the triglycerides produced by the presently described process contain at least 80% and more preferably at least 90% CLA derived acyl groups. The purity of the CLA content may be confirmed via Nuclear Magnetic Resonance Spectroscopy.

In accordance with the above discussion, additional embodiments of the present technology also include the compositions of 1,2 and 1,3 fatty acid diglycerides, specifically 1,2- and 1,3-diglyceride esters of CLA, produced by the above processes, as well as the triglyceride esters of fatty acids. More specifically, embodiments of the present technology include, for example, the triglyceride esters of CLA, including the triglyceride esters of cis-9, trans-11 and trans-10, cis-12 CLA.

EXAMPLES

Example One

Utilizing a conventional process for production of triglyceride, a mixture of caprylic and capric fatty acids (225 g) and glycerol (43.5 g) were circulated through a packed column containing immobilized *Rhizomucor miehei* (10 g) maintained at 60° C. Water of reaction was removed throughout the reaction. After 219 hours, the product was found to contain 93% triglycerides.

One of ordinary skill in the art will appreciate that production according to this conventional process is industrially impracticable and inefficient. Reaction times of upwards of 200 hours are difficult to utilize in an industrial application. High energy costs, low efficiency, and low vessel utilization make this conventional process expensive and time-consuming.

Example Two

A mixture of caprylic and capric fatty acids (225 g) and glycerol (43.5 g) were circulated through a packed column containing immobilized *Rhizomucor miehei* maintained at 60° C., then heated to 100° C. Water of reaction was removed throughout the reaction. The product was found to contain 93% triglycerides after 17 hours.

Example Three

Conjugated linoleic acid (110 lbs) and glycerol (20.8 lbs) were circulated through a packed column containing 2.9 lbs of Lipozyme RM-IM (Novozyme Co.). The column was maintained at 65° C. After exiting the column, the reaction mixture was heated to 110° C., then cooled and returned to the packed column for further reaction. Water of reaction was removed continually throughout the reaction. After about 36 hours, the reaction was complete.

Example Four

A mixture of caprylic and capric fatty acids (225 g), glycerol (43.5 g), and *Rhizomucor miehei* were stirred at 10 mmHg and 45° C. in a batch-type reactor, then the resulting glycerides and any unreacted acids and glycerol were circulated through a reaction zone heated to 100° C. The product was found to contain 93% triglycerides after 17 hours.

Those of ordinary skill in the art will appreciate that the processes of Examples Two through Four, done according to the present technology, offer drastically improved process efficiency. The reaction times of 36 hours in Example 3, and 17 hours in Example 2 and Example 4, are much shorter than conventional reaction times for triglycerides, particularly the 219 hours of Comparative Example 1. Due to the increased efficiency and shorter reaction times, embodiments of the present technology offer increased vessel utilization and decreased energy requirements, both providing a significant cost savings. The increased efficiency and shorter reaction times of the present technology also provide an industrially practicable process for the production of triglycerides.

The invention is now described in such full, clear, concise and exact terms as to enable any person skilled in the art to which it pertains, to practice the same. It is to be understood that the foregoing describes preferred embodiments and examples of the invention and that modifications may be made therein without departing from the spirit or scope of the invention as set forth in the claims.

What is claimed is:

1. A process for preparing triglyceride esters of fatty acids comprising the steps of:

(a) circulating a reaction mixture comprising glycerol, glycerides, or mixtures thereof in combination with fatty acids, fatty acid derivatives, or mixtures thereof at least once through an enzymatic reaction zone A, wherein the enzymatic reaction zone A is maintained at a temperature in the range of about 35° C. to 70° C. and comprises an enzymatic catalyst, to obtain a mixture enriched in 1,3-diglycerides;
    (b) circulating the mixture enriched in 1,3-diglycerides at least once through a thermal reaction zone B maintained at a temperature at least 20° C. greater than that of enzymatic reaction zone A to thereby obtain a mixture enriched in 1,2-diglycerides; and
    (c) re-circulating the mixture enriched in 1,2-diglycerides at least one time through the enzymatic reaction zone A to produce a final product enriched in triglycerides, wherein the total circulation time through reaction zones A and B is less than 48 hours.

2. The process according to claim 1, wherein the process further comprises the step of removing non-glyceride reaction by-products from zones A or B.

3. The process according to claim 1, wherein a lipase is utilized for the enzymatic catalyst.

4. The process according to claim 3, wherein the lipase is supported on a non-reactive matrix.

5. The process according to claim 3, wherein the lipase is selected from the group consisting of: *Rhizomucor miehi, Candida Antarctica, Candida cylindracea, Pseudomonas cepacia, Pseudomonas fluorescens, Candida rugosa, Aspergillus niger,* and *Geotrichum candidum.*

6. The process according to claim 3, wherein the lipase is a 1,3-specific lipase.

7. The process according to claim 1, wherein the mole ratio of the fatty acids or fatty acid derivatives to the glycerol is about 0.5:1 to 3.5:1.

8. The process according to claim 1, wherein the fatty acids or derivatives thereof are conjugated fatty acids or derivatives thereof.

9. A process according to claim 8, wherein the conjugated fatty acids or derivatives thereof are conjugated linoleic acids or derivatives thereof.

10. The process according to claim 9, wherein the conjugated linoleic acids or derivatives thereof are enriched with cis-9, trans-11 or trans-10, cis-12-conjugated linoleic acid isomers.

11. A composition of glyceride esters of fatty acids made by the process of claim 1.

12. The composition according to claim 11, wherein the glyceride esters of fatty acids are conjugated fatty acid glycerides.

13. The composition according to claim 12, wherein the conjugated fatty acid glycerides are conjugated linoleic acid glycerides.

14. The composition according to claim 13, wherein the conjugated linoleic acid glycerides are enriched with cis-9, trans-11 or trans-10, cis-12-conjugated linoleic acid isomers.

15. The process according to claim 1, wherein the final product contains at least 90% by weight triglycerides.

* * * * *